United States Patent [19]

Daffern

[11] 4,279,509
[45] Jul. 21, 1981

[54] ZERO VOLUME FLOW CELL

[75] Inventor: George M. Daffern, Sunnyvale, Calif.

[73] Assignee: Syva Company, Palo Alto, Calif.

[21] Appl. No.: 100,587

[22] Filed: Dec. 5, 1979

[51] Int. Cl.³ .................... G01N 21/05; G01N 21/13
[52] U.S. Cl. .................................. 356/246; 356/410
[58] Field of Search ............... 356/246, 410, 411, 440; 250/576

[56] References Cited

U.S. PATENT DOCUMENTS

| | | | |
|---|---|---|---|
| 3,554,226 | 1/1971 | Robbins | 137/559 |
| 3,636,751 | 1/1972 | Pasini et al. | 73/38 |
| 3,646,313 | 2/1972 | Gorgone et al. | 219/200 |
| 3,647,304 | 3/1972 | Emmel et al. | 356/246 |
| 3,649,829 | 3/1972 | Randolph | 356/410 X |
| 3,714,445 | 1/1973 | Blachere et al. | 356/246 |
| 3,740,158 | 6/1973 | Bellinger et al. | 356/246 |
| 3,822,947 | 7/1974 | Aday, Jr. | 356/246 |
| 3,917,404 | 11/1975 | Heiss | 250/576 X |
| 3,926,526 | 12/1975 | Weiss | 356/246 |
| 3,999,861 | 12/1976 | Bellinger | 356/246 X |
| 4,006,990 | 2/1977 | Munk | 356/246 |
| 4,008,397 | 2/1977 | Zdrodowski | 250/373 |
| 4,021,123 | 5/1977 | Atwood et al. | 356/246 |
| 4,027,983 | 6/1977 | Abrahams | 356/246 |
| 4,141,954 | 2/1979 | Shigetomi | 356/246 X |

*Primary Examiner*—Vincent P. McGraw
*Attorney, Agent, or Firm*—Bertram I. Rowland

[57] ABSTRACT

A flow cell for optical analysis of a fluid sample has a cell chamber whose volume is not limited by considerations of fluid residue carryover. A piston movable within the viewing region and having a conduit through its face is used to collapse the volume of the viewing region to substantially zero while maintaining a flow path between inlet and outlet conduits so that residue can be removed from the flow cell and its conduits with a minimum of cleaning fluid.

10 Claims, 1 Drawing Figure

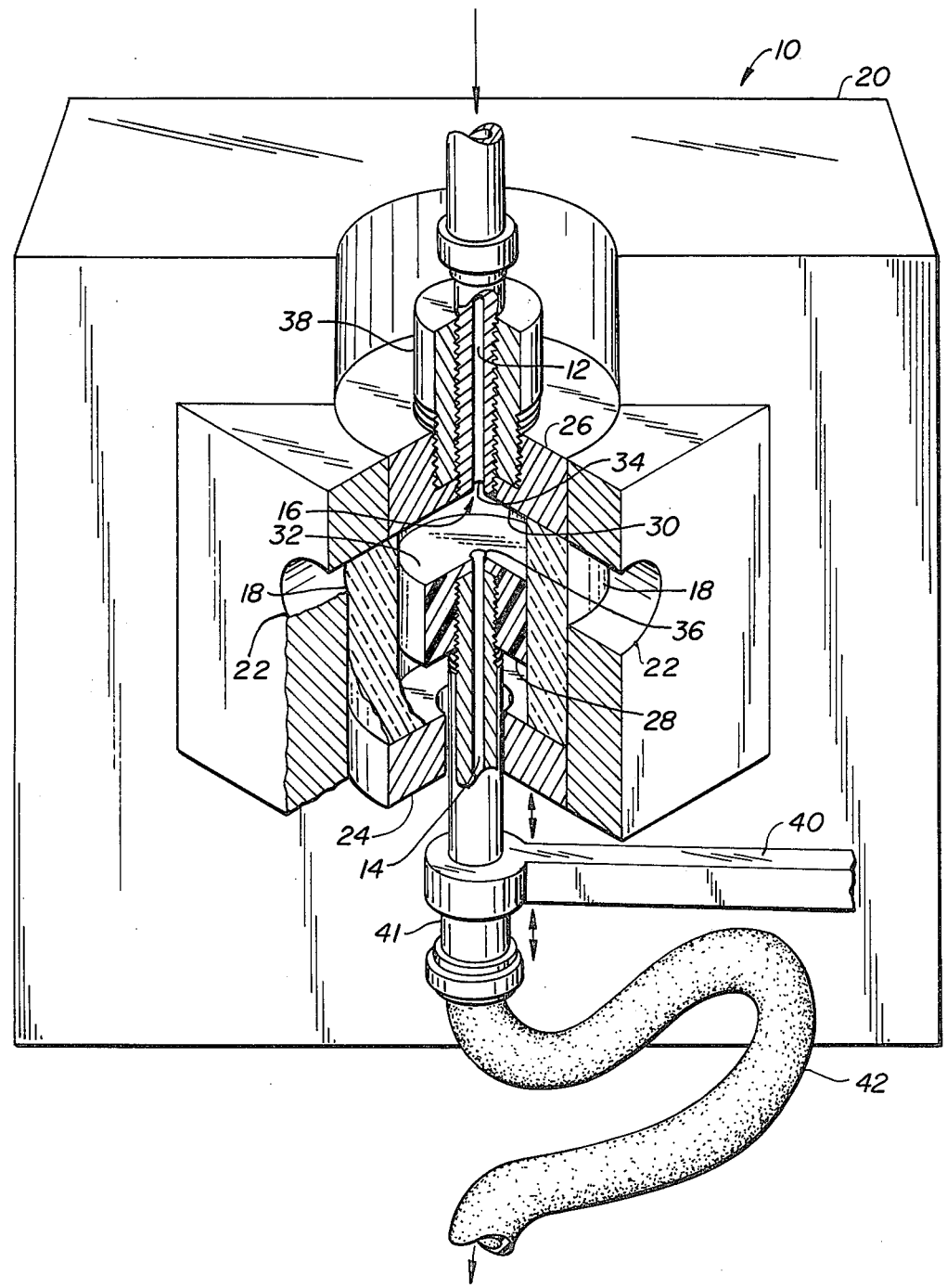

ZERO VOLUME FLOW CELL

BACKGROUND OF THE INVENTION

1. Field of Invention

The invention relates to a flow cell for liquid chromatography, fluorometry and the like wherein optical radiation is directed through a sample within the flow cell and viewed by an optical detector for light absorption or fluorescence.

A flow cell is a device for use in a fluid analysis system such as chromatograph or a fluorometer. Commonly, the cross-sectional dimension of the fluid path is one millimeter or less in order to accommodate the extremely small volumes of liquid which are to be analyzed. In fact, it is desirable to achieve liquid homogeneity with less than one-half milliliter volume. It is also desirable to maximize the volume of the viewing area in order to enhance the yield of detected signals for such small volumes. Certain fixed geometries for flow cells severely limit shape and size. For example, if it is desired to view a sample transverse to the normal flow path, it is necessary to provide a viewing area in a flow cell which is of substantially larger diameter than the diameters of the respective inlets and outlets. The cross-sectional areas of the inlets and outlets are of course restricted to limit the volume of material resident in inlet and outlet conduits. One common geometry includes a cylindrical chamber having an inlet and outlet with inner diameter substantially smaller than the inner diameter of the chamber.

A major problem in the use of flow cells is the phenomenon of carryover. Carryover is the residue of a preceding portion remaining in a flow cell at the time of the next detection cycle which causes errors in signal output. In order to minimize carryover, a flow cell is typically flushed with a cleaning solution between samples. A sharp boundary transition between the inlet orifice and the flow cell viewing chamber gives rise to eddies in fluids moving through the chamber such that the chamber is not adequately clean when flushed with a cleaning solution. Even copius amounts of cleaning solution may be inadequate to eliminate carryover. One partial resolution has been the provision of a countersunk inlet orifice and a deflector in the inlet to create turbulence in the inflowing cleaning solution. These expedients have been only partially successful and have imposed practical limitations on the maximum diameter of the flow cell.

Another problem has been inordinately long thermal equilibration times. The flow cell itself has in the past been used as an equilibration chamber wherein a portion of the walls of the chamber includes a heating element. The minimum achievable time of equilibration is limited because only a portion of the fluid is adjacent the heating element in the flow cell, since a substantial portion of the flow cell must be devoted to window space for a nonthermally conductive window. An alternative technique for achieving more rapid equilibration is desirable to decrease equilibration times.

There is a need for a flow cell having a size and geometry which maximizes signal yield and minimizes carryover. There is also needed a flow cell which requires a minimal amount of cleaning solution for flushing the viewing chamber and for clearing the inlet and outlet conduits.

2. Brief Description of the Prior Art

The following patents are of interest for showing flow cell designs:

Gorgone et al., U.S. Pat. No. 3,646,313 for TEMPERATURE CONTROLLED FLOW CELL;

Emmel et al., U.S. Pat. No. 3,647,304 for MICROVOLUME FLOW CELL;

Bellinger et al., U.S. Pat. No. 3,740,158 for FLOW CELL;

Aday, Jr., U.S. Pat. No. 3,822,947 for FLUID SAMPLE FLOW CELL;

Heiss, U.S. Pat. No. 3,917,404 for FLUOROMETER ASSEMBLY INCLUDING A FLOW CELL;

Munk, U.S. Pat. No. 4,006,990 for CONVERGENT LIGHT ILLUMINATED FLOW CELL FOR LIQUID CHROMATOGRAPHY;

Zdrodowski, U.S. Pat. No. 4,008,397 for FLUOROMETER FLOW CELL; and

Shigetomi, U.S. Pat. No. 4,141,954 for REACTION TUBE ASSEMBLY FOR AUTOMATIC ANALYZER.

SUMMARY OF THE INVENTION

A flow cell for optical analysis of a fluid sample has a cell chamber whose volume is not limited by considerations of carryover. The flow cell includes a fluid flow path through an enclosed optical viewing region or chamber, a first fluid access means or conduit coupled to the viewing region, a second fluid access means or conduit to the viewing region and piston means with a conduit through its face and movable within the viewing region for collapsing the volume of the viewing region to substantially zero while maintaining the fluid flow path between the two conduits such that the collapsing means can mechanically clear the viewing region of fluid residue and the remaining flow path can be flushed by a minimal volume of a suitable cleaning solution.

In a specific embodiment, one of the conduits is provided through the face of the piston and is adapted to abut to an opposing face of the viewing region such that the two conduits form a substantially continuous flow path.

In a further specific embodiment, means are provided adjacent the fluid inlet conduit for heating the sample fluid to equilibration prior to entry into the viewing area.

It is an object of this invention to provide a flow cell for small volume samples wherein the viewing area can be reduced to substantially zero volume such that fluid conduits into and out of the view area can be flushed with a minimal amount of cleaning solution.

It is a further object of this invention to provide means for mechanically sweeping the viewing chamber of sample residue.

It is a still further object of the invention to provide means for preheating a sample to be tested to equilibration prior to entry into the viewing chamber.

The further objects and advantages of the invention will become more apparent from the detailed description which follows when considered in connection with the accompanying drawings.

BRIEF DESCRIPTION OF THE DRAWINGS

FIG. 1 is a perspective view in partial cross-section of a flow cell according to the invention.

DETAILED DESCRIPTION OF PREFERRED EMBODIMENTS

Referring to FIG. 1 there is shown a flow cell 10 having an inlet conduit 12, an outlet conduit 14, a viewing chamber 16 and optical viewing windows 18. The flow cell 10 is typically mounted in a fluorometer or chromatograph (not shown). Accordingly, an appropriate mounting jig 20 is provided with viewing ports 22 oriented to view a sample within the chamber 16 through viewing windows 18. The windows 18 are held in place by frame pieces 24 and 26, one of which may also serve as a wall to the chamber 16.

According to the invention, means are provided for collapsing the chamber 16 to zero volume such that a minimum volume fluid flow path is designated between the inlet conduit 12 and the outlet conduit 14. For this purpose, a piston 28 with a fluid conduit therethrough is provided within the chamber 16 which intimately mates with the walls of the chamber 16 and is movable therein. The chamber 16 forming the viewing area preferably comprises a hollow right circular cylinder defined by the windows 18 formed of quartz and enclosed by a flat end face 30 and an opposing piston face 32 of piston 28 in a first position. The end face 30 mates with the opposing piston face 32 to abut intimately in a second position of substantially zero chamber volume. Movement of the piston 28 from the first position of maximum chamber volume to the second position of minimum (zero) volume mechanically sweeps the inner surface of the windows 18 of residue. In the second position, a chamber entry orifice 34 of conduit 12 mates with a chamber exit orifice 36 of conduit 14, the entry orifice 36 in the piston end face 32 being directly aligned with the chamber entry orifice 34 in the opposing cylinder face 30.

A heating element 38 is provided concentric about the inlet conduit 12. The heating device 38 may be a Peltier unit impinging upon the conduit 12 along a length of the conduit 12. The volume of a sample to be furnished to the viewing area can be preheated to equilibration prior to its introduction into the viewing chamber 16. The heating element 38 may be extended along the inlet conduit 12 so the corresponding internal fluid volume of the conduit 12 is substantially the volume of the fully expanded viewing chamber 16. The entire sample to be analyzed may then be simultaneously preheated.

Means are provided for moving the piston 28 reciprocally within the viewing chamber 16. For this purpose, a push rod 40 may be employed in connection with a reciprocating drive mechanism (not shown). A piston connector rod 41 formed around the conduit 14 must therefore be sufficiently rigid so that the force of movement of the connecting rod 40 can be transmitted to the piston 28. A flexible coupling is provided in the conduit 14, for example silicone rubber tubing 42. The rubber tubing 42 should be sufficiently flexible and long to allow reasonable freedom of reciprocal movement of the piston 28.

It is important that the piston 28 make an intimate seal with the inside of the windows 18 so that the piston 28 can effectively sweep windows 18 clean of residue. For this purpose, the windows 18 are preferably quartz with polished inner surfaces, and the piston 18 is preferably constructed of Teflon, that is, polytetrafluoroethylene, having polished side surfaces matching the polished surfaces of the windows 18. The conduits 12 and 14 are preferably stainless steel, and the flow paths have an inner diameter of less than about one millimeter and preferably less than about 0.2 millimeter. The small diameter accommodates the relatively small volume of sample to be analyzed.

In operation, the piston 28 is opened to a first position allowing an adequate volume for viewing through windows 22 into the view area 16. A sample is introduced through conduit 12 and preheated to equilibration by heating element 38. Thereafter, the sample is supplied to the viewing area 16 where it can be optically analyzed. Upon completion of analysis, the sample is forced from the chamber of viewing area 16 out through conduit 14. The piston 28 is urged to a second position having piston face 32 intimately abutting to opposing cylinder face 30 by movement of connecting rod 40. The residue of the sample is thereby mechanically swept from the viewing chamber 16. Thereafter, a cleaning solution is flushed through conduit 12 and conduit 14 to clear sample residue from the conduits. The piston 28 is thereafter withdrawn to the first position and the next sample is introduced.

The invention has now been explained with reference to specific embodiments. Other embodiments will be suggested to those of ordinary skill in the appropriate art upon review of the present specification. It is therefore not intended that the invention be limited except as indicated by the appended claims.

What is claimed is:

1. A flow cell apparatus having a fluid flow path through an enclosed optical viewing region having optical viewing windows, said flow cell comprising:
   first fluid access means to said viewing region;
   second fluid access means to said viewing region; and
   means having a conduit therethrough and movable within said viewing region for collapsing said viewing region to substantially zero volume while maintaining said fluid flow path between said first fluid access means and said second fluid access means such that said collapsing means can clear said viewing region of fluid and said flow path can be flushed by a minimal volume of a cleaning fluid.

2. The flow cell apparatus as claimed in claim 1 wherein said enclosed optical viewing region is defined by a cylinder having walls formed by a window member and wherein said collapsing means comprises a piston mated to said cylinder.

3. The flow cell apparatus as claimed in claim 2 wherein said piston has a face adapted to abut intimately to an opposing face of said cylinder in a closed position defining zero volume and wherein said first fluid access means comprises a first orifice in said cylinder face and said second fluid access means comprises a second orifice in said piston face, said second orifice being in fluid communication with said conduit and wherein said first orifice mates to said second orifice in said closed position.

4. The flow cell apparatus as claimed in claim 3 wherein said piston is right circularly cylindrical, said cylinder is hollow right circularly cylindrically complementary to said piston, and wherein said conduit is coaxially disposed through said piston.

5. The flow cell as claimed in claim 4 wherein said piston is formed of polytetrafluoroethylene.

6. The flow cell as claimed in claim 4 wherein said cylinder is formed of quartz.

7. The flow cell as claimed in claim 4 wherein said first access means and said second access means each have an inside diameter of less than about 1.0 millimeter.

8. The flow cell as claimed in claim 7 wherein said first access means and said second access means each have an inside diameter of less than about 0.2 millimeter.

9. The flow cell as claimed in claim 1 further including means adjacent said fluid access means at the inlet end of said flow cell for heating fluid to be introduced through said fluid access means into said optical viewing region.

10. A method for clearing a flow cell formed of a cylinder of fluid residue comprising:
  urging a piston having a fluid access port in the piston within said cylinder from a first maximum volume position to a second substantially zero volume position to sweep said fluid residue from walls of said cylinder and to mate said piston fluid access port with a cylinder fluid access port; and
  flushing said residue through said access ports with a cleaning fluid.

* * * * *